United States Patent [19]

Kühle et al.

[11] 4,344,962

[45] Aug. 17, 1982

[54] SULPHENYLATED ACYLURETHANES AND THEIR USE AS FUNGICIDES

[75] Inventors: Engelbert Kühle, Bergisch Gladbach; Wilfried Paulus; Hermann Genth, both of Krefeld; Wilhelm Brandes, Leichlingen, all of Fed. Rep. of Germany

[73] Assignee: Bayer Aktiengesellschaft, Leverkusen, Fed. Rep. of Germany

[21] Appl. No.: 184,676

[22] Filed: Sep. 8, 1980

[30] Foreign Application Priority Data

Sep. 20, 1979 [DE] Fed. Rep. of Germany ....... 2938111

[51] Int. Cl.³ ................... C07C 145/02; A01N 47/20
[52] U.S. Cl. ........................................ 424/300; 560/9; 260/545 R; 564/102; 71/67
[58] Field of Search ................ 560/9, 24; 424/300; 71/67

[56] References Cited

U.S. PATENT DOCUMENTS

3,236,842  2/1966  Klauke .............................. 424/309
3,406,192  10/1968 Speziale ............................. 560/24
3,642,863  2/1972  Speziale et al. ..................... 260/471

*Primary Examiner*—Michael L. Shippen
*Attorney, Agent, or Firm*—Sprung, Horn, Kramer & Woods

[57] ABSTRACT

A sulphenylated acylurethane of the formula

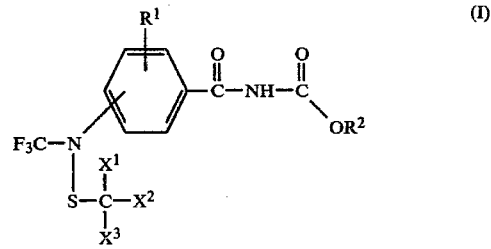

wherein
$R^1$ denotes hydrogen, halogen, nitro, alkyl, alkoxy or halogenomethyl,
$R^2$ denotes alkyl, alkenyl, alkinyl, cycloalkyl or aralkyl and
$X^1$, $X^2$ and $X^3$ are identical or different and denote halogen; a process for its preparation by contacting an isocyanate of the formula

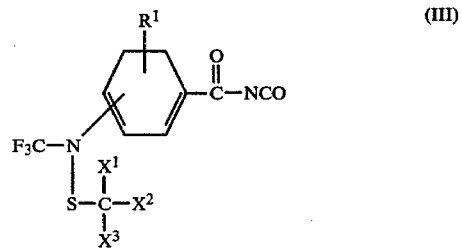

wherein
$R^1$, $X^1$, $X^2$ and $X^3$ have the abovemeaning with a hydroxy compound of the formula $R^2$-OH                                                          (IV)

wherein
$R^2$ has the abovemeaning in the presence of a diluent.

The novel sulphenylated acylurethanes are useful as microbicidal agents to protect industrial materials against degradation.

6 Claims, No Drawings

SULPHENYLATED ACYLURETHANES AND THEIR USE AS FUNGICIDES

The invention relates to new sulphenylated acylurethanes, a process for their preparation and their use as microbicides.

New sulphenylated acylurethanes of the formula

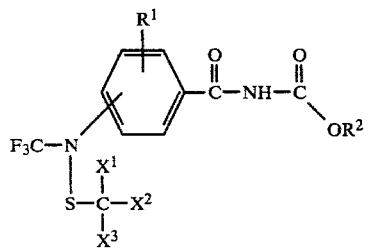

(I)

wherein
$R^1$ denotes hydrogen, halogen, nitro, alkyl, alkoxy or halogenomethyl,
$R^2$ denotes alkyl, alkenyl, alkinyl, cycloalkyl or aralkyl and
$X^1$, $X^2$ and $X^3$ are identical or different and denote halogen, have been found.

According to the invention, halogen can denote fluorine, chlorine, bromine or iodine. Halogen can preferably be fluorine or chlorine. Halogenomethyl can preferably be trifluoromethyl or trichloromethyl.

According to the invention, alkyl can denote a straight-chain or branched hydrocarbon radical which has 1 to 6 carbon atoms and can optionally be interrupted by a hetero-atom (O, S or N-alkyl). A lower alkyl radical with up to about 6 carbon atoms may be mentioned as preferred. Examples of alkyl are methyl, ethyl, propyl, iso-propyl, butyl, iso-butyl, pentyl, iso-pentyl, hexyl, iso-hexyl, dimethylaminoethyl, 2-methoxyethyl and 2-ethylmercaptoethyl.

According to the invention, alkenyl can denote a straight-chain or branched hydrocarbon radical with 3 to 12 carbon atoms. A lower alkenyl radical with up to about 6 carbon atoms may be mentioned as preferred. Examples of alkenyl are allyl, propenyl, iso-propenyl, butenyl, iso-butenyl, pentyl, iso-pentenyl, hexenyl and iso-hexenyl.

According to the invention, alkinyl can denote a straight-chain or branched hydrocarbon radical with 3 to 12 carbon atoms. A lower alkenyl radical with up to about 6 carbon atoms may be mentioned as preferred. Examples of alkinyl are propinyl, iso-propinyl, butinyl, iso-butinyl, pentinyl, iso-pentinyl, hexinyl and iso-hexinyl.

According to the invention, cycloalkyl can denote a cyclic hydrocarbon radical with 5 to 8 carbon atoms. The cyclopentyl radical and the cyclohexyl radical are preferred.

According to the invention, aralkyl can denote a straight-chain or branched hydrocarbon radical with up to 6 carbon atoms, in the aliphatic part, and phenyl in the aromatic part.

The benzyl radical may be mentioned as an example.

According to the invention, alkoxy can be derived from a straight-chain or branched aliphatic alcohol with 1 to 12 carbon atoms. The lower alkoxy radical with up to about 6 carbon atoms may be mentioned as preferred. Examples of alkoxy are methoxy, ethoxy, propoxy, iso-propoxy, butoxy, iso-butoxy, pentoxy, iso-pentoxy, hexyloxy and iso-hexyloxy. Preferred alkoxy is methoxy.

Preferred new sulphenylated acylurethanes according to the invention are compounds of the formula

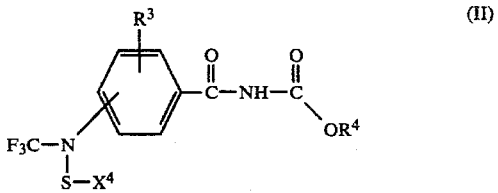

(II)

wherein
$R^3$ denotes hydrogen, chlorine, nitro, lower alkyl, lower alkoxy or trifluoromethyl,
$R^4$ denotes lower alkyl, lower alkenyl or benzyl and
$X^4$ denotes trifluoromethyl, trichloromethyl, fluorodichloromethyl or difluoro-chloromethyl.

The following new sulphenylated acylurethanes may be mentioned specifically: 2-, 3- or 4-N(fluorodichloromethylmercapto)N-trifluoromethylamino-benzoyl-N'-methylurethane, -N'-ethylurethane, -N'-tert.-butylurethane, -N'-allylurethane, -N'-propargylurethane, -N'-cyclohexylurethane, -N'-benzylurethane,-N'-2-methoxyethylurethane, -N'-2-ethylmercaptoethylurethane and -N'-2-dimethylamino-ethylurethane, 2-N-(trifluoromethylmercapto)N-trifluromethylaminobenzoyl-N'-methylurethane, 2-N(fluorodichloromethylmercapto)N-trifluoromethylaminobenzoyl-4-chloro-N'-methylurethane and 2-N(fluorodichloromethyl-mercapto)-N-trifluoromethylamino-5-trifluoromethylbenzoyl-N'-methylurethane.

Furthermore, a process has been found for the preparation of sulphenylated acylurethanes, which is characterised in that acyl isocyanates of the formula

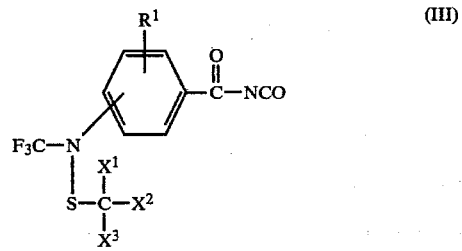

(III)

wherein
$R^1$, $X^1$, $X^2$ and $X^3$ have the meaning indicated above, are reacted with a hydroxy compound of the formula $$R^2\text{-OH}$$ (IV)

wherein
$R^2$ has the meaning indicated above, in the presence of a diluent.

The process according to the invention can be illustrated with the aid of the following equation:

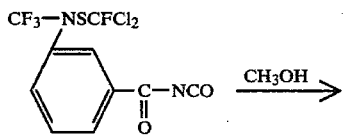

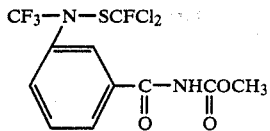

Acylisocyanates of the formula (III) can be prepared by reacting carboxylic acid amides of the formula

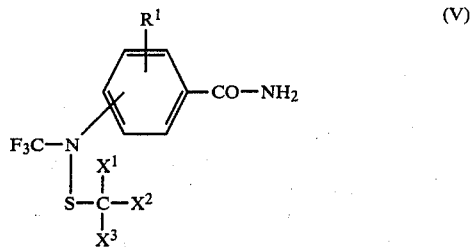

wherein
R$^1$, X$^1$, X$^2$ and X$^3$ have the abovementioned meaning, with oxalyl chloride in an inert diluent, such as an ether, a hydrocarbon or a halogenated hydrocarbon.

Acylisocyanates of the formula

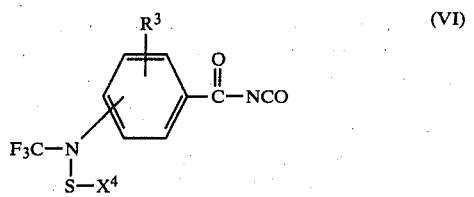

wherein
R$^3$ and X$^4$ have the abovementioned meaning, may be mentioned as preferred.

The following acylisocyanates may be mentioned as examples: 2-, 3- or 4-N-(fluorodichloromethylmercapto)-N-trifluoromethylaminobenzoyl isocyanate, 2-N-(trifluoromethylmercapto)-N-trifluoromethylaminobenzoyl isocyanate, 2-N-(fluorodichloromethylmercapto)N-trifluoromethylamino-4-chlorobenzoyl isocyanate and 2-N-(fluorodichloromethylmercapto)-N-trifluoromethylamino-5-trifluoromethylbenzoyl isocyanate.

Hydroxy compounds for the process according to the invention are in themselves known. Hydroxy compounds of the formula

R$^4$-OH (VII)

wherein
R$^4$ has the abovementioned meaning, can preferably be employed in the process according to the invention.

The following hydroxy compounds may be mentioned as examples: methanol, ethanol, isopropanol, tert.butanol, dimethylaminoethanol, 2-ethylmercaptoethanol, 2-methoxy-ethanol, allyl alcohol, propargyl alcohol, cyclohexanol, benzyl alcohol, 4-chlorobenzyl alcohol and phenylethanol.

Diluents which may be mentioned are all the inert solvents which do not react with the reactants under the reaction conditions. For example ethers, such as diethyl ether or dioxane, hydrocarbons, such as toluene, and chlorinated hydrocarbons, such as chlorobenzene or chloroform, mentioned. It is also possible to carry out the reaction in an excess of the appropriate hydroxy compound. The process according to the invention is in general carried out in the temperature range from 0° to 100° C., preferably 20° to 50° C.

The process according to the invention is in general carried out under normal pressure. However, it is possible to carry out the process under reduced pressure or increased pressure. Generally a pressure of about 0.2 bar to about 100 bar is suitable.

The new sulphenylated acylurethanes according to the invention are compounds with a particularly powerful microbicidal action. They can be used, for example, for protecting industrial materials against microbial degradation or against a change caused by microorganisms, and for protecting wood.

Examples of industrial materials are adhesives, size, paper and cardboard, textiles, leather, wood, paints, plaster and vessel contents which can be damaged or destroyed by microbial action. The active compounds according to the invention are particularly suitable for the preparation of fungicidal paints and impregnating agents.

Examples of microorganisms which can cause degradation of or change in industrial materials are bacteria, yeasts, fungi and algae.

Examples of bacteria, yeasts, fungi and algae which may be mentioned are: *Alternaria tenuis, Aspergillus niger, Chaetomium globosum, Coniophora cerebella, Lentinus tigrinus, Pullularia pullulans, Penicillium glaucum, Staphylococcus aureus, Candida albicans, Trichophyton pedis, Stichococcus bacillaris Naegeli, Euglena gracilis Klebs, Chlorella pyrenoidosa* and *Enteromorpha intestinalis.*

The new sulphenylated acylurethanes according to the invention have a particularly powerful fungicidal action.

The new sulphenylated acylurethanes according to the invention can be converted into the customary formulations, such as solutions, emulsions, suspensions, powders, pastes and granules, depending on their field of use. These formulations can be prepared in a manner which is in itself known, for example by mixing the active compounds with an extender which from liquid solvent and/or solid carriers, if appropriate using surface-active agents, such as emulsifiers and/or dispersing agents, it being possible, for example in the case where water extenders are used, optionally to use organic solvents as auxiliary solvents.

The active compounds according to the invention can be present in the formulations as mixtures with other known active compounds. The following active compounds may be mentioned as examples: benzimidazolyl methylcarbamate, tetramethyl-thiuram disulphide, N-fluorodichloromethylthiophthalimide and N,N-dimethyl-N'-phenyl-(N'fluorodichloromethylthio)-sulphamide.

The use form of the microbicidal agent according to the invention in general contains from 90 to 10% by weight, preferably from 50 to 15% by weight, of sulphenylated acylurethane as the active compound.

The concentration of active compound in ready-to-use formulations can be varied within wide limits. In general, it is in the range from 0.03 to 3% by weight, preferably in the range from 0.3 to 1.5% by weight, relative to the total amount of the formulation.

PREPARATION EXAMPLES

EXAMPLE 1

(3[N(Dichloro-fluoro-methylmercapto)-N-trifluoromethyl]amino-benzoyl-methylurethane)

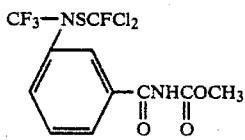

11.7 g of 3-N(dichlorofluoromethylmercapto)-N-trifluoromethylaminobenzoyl isocyanate were dissolved in 100 ml of toluene at room temperature and 10 ml of methanol were added. During this addition, the temperature rises to 33° C. The mixture is concentrated in vacuo and the residue is recrystallized from wash benzine. Melting point: 104° C., 11 g.

The following Examples 2 to 5 are carried out analogously to Example 1.

| Example | Product | Melting point |
|---|---|---|
| 2 | 3-[N(Dichloro-fluoro-methylmercapto)-N-trifluoromethyl]aminobenzoyl-isopropyl-urethane | 112° C. |
| 3 | 3-[N(Dichloro-fluoro-methylmercapto)-N-trifluoromethyl]aminobenzoyl-n-propyl-urethane | 92° C. |
| 4 | 3-[N(Dichloro-fluoro-methylmercapto)-N-trifluoromethyl]aminobenzoyl-allyl-urethane | 95° C. |
| 5 | 3-[N(Dichloro-fluoro-methylmercapto)-N-trifluoromethyl]aminobenzoyl-n-butyl-urethane | 95° C. |

EXAMPLE 6

(2-[N-Dichloro-fluoro-methylmercapto)-N-trifluoromethyl]-aminobenzoyl-methyl-urethane)

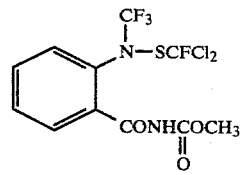

14 g of 2-N-(dichlorofluoromethylmercapto)-N-trifluoromethylaminobenzoyl isocyanate are added dropwise to 50 ml of methanol. Only a weak reaction can be detected during this addition. The mixture is stirred at 50° C. for some time and concentrated in vacuo and the residue is recrystallized from ethyl acetate/petroleum ether. 10 g of the above product of melting point 115° C. are obtained.

The following Examples 7 to 15 are carried out analogously to Example 6:

| Example | Product | Melting point (refractive index) $n_D^{20}$ |
|---|---|---|
| 7 | 2-[N(Dichloro-fluoro-methylmercapto)-N-trifluoromethyl]aminobenzoyl-isopopyl-urethane | 65° C. |
| 8 | 2-[N(Dichloro-fluoro-methylmercapto)-N-trifluoromethyl]aminobenzoyl-allyl-urethane | (1.5263) |
| 9 | 2-[N(Dichloro-fluoro-methylmercapto)-N-trifluoromethyl]aminobenzoyl-n-butyl-urethane | 92° C. |
| 10 | 2-[N(Dichloro-fluoro-methylmercapto)-N-trifluoromethyl]aminobenzoyl-benzyl-urethane | 111° C. |
| 11 | 3-[N(Dichloro-fluoro-methylmercapto)-N-trifluoromethyl]amino-4-chlorobenzoyl-n-propyl-urethane | 107° C. |
| 12 | 3-[N(Dichloro-fluoro-methylmercapto)-N-trifluoromethyl]amino-4-chlorobenzoyl-allyl-urethane | 91° C. |
| 13 | 4-[N(Dichloro-fluoro-methylmercapto)-N-trifluoromethyl]aminobenzoyl-methyl-urethane | 98° C. |
| 14 | 4-[N(Dichloro-fluoro-methylmercapto)-N-trifluoromethyl]aminobenzoyl-n-butyl-urethane | 131° C. |
| 15 | 4-[N(Dichloro-fluoro-methylmercapto)-N-trifluoromethyl]aminobenzoyl-benzyl-urethane | 118° C. |

USE EXAMPLES

EXAMPLE 16

The activity of the substance according to Example 1 against fungi is tested in comparison with N,N-dimethyl-N'-phenyl-N'-(fluorodichloromethylthio)sulphamide. For this, the minimum inhibitory concentrations (MIC) are determined as follows:

The active compound, according to the invention, of Example 1 and the comparison substance are added, in concentrations of 0.5 mg/l to 5,000 mg/l, to a nutrient medium prepared from agar, beer wort and peptone. After the agar has solidified, it is contaminated with pure cultures of the test organisms listed in Table 1. After storage at 28° C. and at a relative atmospheric humidity of 60 to 70% for two weeks, the MIC is determined. The MIC is the lowest concentration of active compound at which the species of microbe used does not grow at all. It is indicated in the Table below:

TABLE

Data regarding the MIC values in mg/l for the action of the following active compounds on fungi:

| Test organism | Substance according to Example 1 | Comparison substance |
|---|---|---|
| Alternaria tenuis | 1.5 | 20 |
| Aspergillus niger | 5 | 50 |
| Chaetomium globosum | 3.5 | 20 |
| Cladosporium herbarum | 1.5 | 20 |
| Coniophora cerebella | <0.5 | 10 |
| Penicillium glaucum | 5 | 35 |
| Pullularia pullulans | 0.5 | 20 |
| Trichoderma viride | 15 | 5000 |

EXAMPLE 17

Test for the resistance of paint films to mould:
The test is carried out in accordance with the method described in report 219 of the Defence Standards Laboratories Maribyrnong/Australia, as follows: smooth cardboard is coated on both sides with the product to be tested and the coating is dried to room temperature for 8 days. For ageing, part of the paint film is exposed to running water at 24° C. for 24 hours, another part is exposed to fresh air at 40° to 60° C. for 8 days and a third part is subjected to a dry Xenon test for 110 hours. 5×5 cm pieces cut out of the samples thus prepared are individually placed on a glucose nutrient medium in Petri dishes and are contaminated with a spore suspension of the following fungi: *Aspergillus niger, Pullularia pullulans, Alternaria speciales, Penicillium citrinum, Stachybotrys atra, Paecilomyces varioti, Cladosporium herbarum, Aspergillus ustus* and *Coniophora cerebella*.

The contaminated dishes are stored at 28° to 30° C. and at a relative atmospheric humidity of 90 to 95%, and are evaluated after 3 weeks. Paint films are considered mould-resistant if the samples remain free from fungus after this test.

The resistance to mould of a commercially available gloss paint based on alkyd resin is tested by this test method, after adding 0.6% of 3-[N-(dichlorofluoromethylthio)-N(trifluoromethyl)]aminobenzoyl methylcarbamate (relative to the weight of film).

Result

The paint films remain free from fungus; the active compound neither decomposed nor evaporated under these test conditions.

EXAMPLE 18

The minimum inhibitory concentrations (MIC) of other substances according to the invention are determined, as indicated in Example 3, to demonstrate the activity against fungi. Data regarding the MIC values in mg/l for the action of the following active compounds on fungi:

| Test organisms | Active compound according to Example: | | | | | |
|---|---|---|---|---|---|---|
| | 1 | 4 | 5 | 7 | 9 | 10 | 13 |
| *Alternaria tenuis* | 2 | 0.5 | 2 | 15 | 100 | 5 | 5 |
| *Chaetomium globosum* | 10 | 2 | 10 | 350 | 7.5 | 7.5 | 10 |
| *Cladosporium herbarum* | 2 | 50 | 5 | 20 | 50 | 35 | 10 |
| *Coniophora cerebella* | 0.5 | 0.5 | 0.5 | 0.5 | 0.5 | 0.5 | 0.5 |
| *Pullularia pullulans* | 0.5 | 1.5 | 5 | 350 | 200 | 75 | 5 |

What is claimed is:

1. A sulphenylated acylurethane of the formula

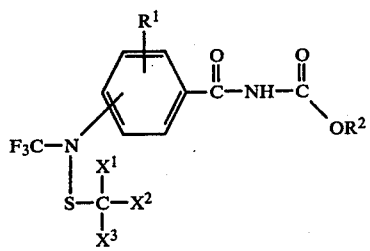

wherein
$R^1$ denotes hydrogen, halogen, nitro, alkyl, alkoxy or halogenomethyl,
$R^2$ denotes alkyl, alkenyl, alkinyl, cycloalkyl or aralkyl and
$X^1$, $X^2$ and $X^3$ are identical or different and denote halogen.

2. A sulphenylated acylurethane according to claim 1, of the formula

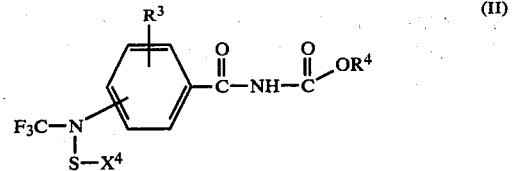

wherein
$R^3$ denotes hydrogen, chlorine, nitro, lower alkyl, lower alkoxy or trifluoromethyl,
$R^4$ denotes lower alkyl, lower alkenyl or benzyl and
$X^4$ denotes trifluoromethyl, trichloromethyl, fluorodichloromethyl or difluoro-chloromethyl.

3. A sulphenylated acylurethane according to claim 1 which is (3[N-(Dichloro-fluoro-methylmercapto)-N-trifluoromethyl]-amino-benzoyl-methylurethane).

4. A sulphenylated acylurethane according to claim 1 which is 3-[N(Dichloro-fluoro-methylmercapto)-N-trifluoromethyl]aminobenzoyl-n-propyl-urethane.

5. A fungicidal composition comprising a fungidical effective amount of a compound of the formula

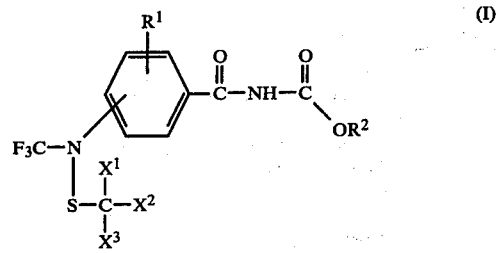

wherein
$R^1$ denotes hydrogen, halogen, nitro, alkyl, alkoxy or halogenomethyl,
$R^2$ denotes alkyl, alkenyl, alkinyl, cycloalkyl or aralkyl and
$X^1$, $X^2$ and $X^3$ are identical or different and denote halogen and a diluent.

6. A method of combating a fungus which comprises applying to locus thereof a fungicidally effective amount of a sulfonated acylurethane of the formula

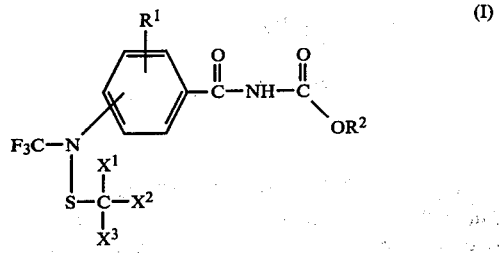

wherein
$R^1$ denotes hydrogen, halogen, nitro, alkyl, alkoxy or halogenomethyl,
$R^2$ denotes alkyl, alkenyl, alkinyl, cycloalkyl or aralkyl and
$X^1$, $X^2$ and $X^3$ are identical or different and denote halogen and a diluent.

* * * * *